United States Patent
Zeng et al.

(10) Patent No.: US 11,919,933 B2
(45) Date of Patent: Mar. 5, 2024

(54) USE OF MYOG GENE AS TARGET IN PREPARATION OF DRUG FOR TREATING CARDIOMYOCYTE APOPTOSIS-ASSOCIATED CARDIOVASCULAR DISEASE

(71) Applicant: GUANGDONG BEATING ORIGIN REGENERATIVE MEDICINE CO., LTD., Foshan (CN)

(72) Inventors: Rong Zeng, Foshan (CN); Bin Lin, Foshan (CN)

(73) Assignee: GUANGDONG BEATING ORIGIN REGENERATIVE MEDICINE CO., LTD., Foshan (CN)

( * ) Notice: Subject to any disclaimer, the term of this patent is extended or adjusted under 35 U.S.C. 154(b) by 0 days.

(21) Appl. No.: 18/053,769

(22) Filed: Nov. 9, 2022

(65) Prior Publication Data

US 2023/0071726 A1  Mar. 9, 2023

Related U.S. Application Data

(63) Continuation of application No. PCT/CN2021/138959, filed on Dec. 17, 2021.

(30) Foreign Application Priority Data

Dec. 21, 2020 (CN) .......................... 202011518860.6

(51) Int. Cl.
| | |
|---|---|
| *G01N 33/53* | (2006.01) |
| *C07K 14/47* | (2006.01) |
| *C12N 5/077* | (2010.01) |
| *C12N 15/86* | (2006.01) |
| *G01N 33/50* | (2006.01) |

(52) U.S. Cl.
CPC ........ *C07K 14/4705* (2013.01); *C12N 5/0657* (2013.01); *C12N 15/86* (2013.01); *G01N 33/5061* (2013.01); *C12N 2503/02* (2013.01); *G01N 2333/4706* (2013.01)

(58) Field of Classification Search
None
See application file for complete search history.

(56) References Cited

U.S. PATENT DOCUMENTS

| | | | |
|---|---|---|---|
| 2015/0297638 A1 | 10/2015 | Ashraf | |
| 2018/0273906 A1 | 9/2018 | Ashraf | |
| 2022/0220174 A1* | 7/2022 | Rassaf | ............... G01N 33/6872 |

FOREIGN PATENT DOCUMENTS

| | | |
|---|---|---|
| CN | 111411075 A | 7/2020 |
| CN | 112608972 A | 4/2021 |

OTHER PUBLICATIONS

Qiang Gao, et al., Myogenin suppresses apoptosis induced by angiotensin II in human induced pluripotent stem cell-derived cardiomyocytes, Biochemical and Biophysical Research Communications, 2021, pp. 84-90, vol. 552.

Shu-Ting Liu, et al., The regulatory mechanisms of myogenin expression in doxorubicin-treated rat cardiomyocytes, Oncotarget, 2015, pp. 37443-37457, vol. 6, No. 35.

Yuanyuan Nie, et al., Research progress on the relationship between cardiomyocyte apoptosis and cardiovascular diseases, Journal of Practical Medicine, 2012, pp. 324-326, vol. 28, No. 2, Eng abstract.

Ruli Li, et al., Irisin ameliorates angiotensin II-induced cardiomyocyte apoptosis through autophagy, Journal of Cellular Physiology, 2019, pp. 1-11.

* cited by examiner

*Primary Examiner* — Michael D Pak

(74) *Attorney, Agent, or Firm* — Bayramoglu Law Offices LLC

(57) ABSTRACT

The present disclosure belongs to the technical field of biomedicine and, particularly, relates to a use of an MYOG gene as a target in the preparation of a drug for treating a cardiomyocyte apoptosis-associated cardiovascular disease (CVD). By constructing angiotensin II-induced human induced pluripotent stem cell-differentiated cardiomyocyte apoptosis models in vitro, the present disclosure reveals for the first time the role of the transcription factor MYOG in the inhibition of cardiomyocyte apoptosis and provides a theoretical and scientific basis for drug research and development of cardiomyocyte apoptosis-associated CVDs. MYOG gene becomes a new target for CVD drug research and development.

1 Claim, 5 Drawing Sheets

Specification includes a Sequence Listing.

DAPI/TUNEL

```
                              SEQUENCE LISTING

Sequence total quantity: 4
SEQ ID NO: 1            moltype = DNA  length = 18
FEATURE                 Location/Qualifiers
misc_feature            1..18
                        note = The sequence is synthetized.
source                  1..18
                        mol_type = other DNA
                        organism = synthetic construct
SEQUENCE: 1
gcccaaggtg gagatcct                                                     18

SEQ ID NO: 2            moltype = DNA  length = 18
FEATURE                 Location/Qualifiers
misc_feature            1..18
                        note = The sequence is synthetized.
source                  1..18
                        mol_type = other DNA
                        organism = synthetic construct
SEQUENCE: 2
ggtcagccgt gagcagat                                                     18

SEQ ID NO: 3            moltype = DNA  length = 20
FEATURE                 Location/Qualifiers
misc_feature            1..20
                        note = The sequence is synthetized.
source                  1..20
                        mol_type = other DNA
                        organism = synthetic construct
SEQUENCE: 3
tgggtgtgaa ccatgagaag                                                   20

SEQ ID NO: 4            moltype = DNA  length = 20
FEATURE                 Location/Qualifiers
misc_feature            1..20
                        note = The sequence is synthetized.
source                  1..20
                        mol_type = other DNA
                        organism = synthetic construct
SEQUENCE: 4
gtgtcgctgt tgaagtcaga                                                   20
```

USE OF MYOG GENE AS TARGET IN PREPARATION OF DRUG FOR TREATING CARDIOMYOCYTE APOPTOSIS-ASSOCIATED CARDIOVASCULAR DISEASE

CROSS REFERENCE TO THE RELATED APPLICATIONS

This application is a continuation application of International Application No. PCT/CN2021/138959, filed on Dec. 17, 2021, which is based upon and claims priority to Chinese Patent Application No. 202011518860.6, filed on Dec. 21, 2020, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBBZ011-PKG-Sequence-Listing.xml, created on 09/22/2022, and is 6,049 bytes in size.

TECHNICAL FIELD

The present disclosure belongs to the technical field of biomedicine and, particularly, relates to a use of the MYOG gene as a target in the preparation of a drug for treating a cardiomyocyte apoptosis-associated cardiovascular disease (CVD).

BACKGROUND

CVDs are currently the biggest threat to human health and are the number one cause of death worldwide. According to statistics of the World Health Organization (WHO), more than 17 million people worldwide die of CVDs every year, accounting for 31% of the total global deaths. The improvement of people's living standards and the change in people's dietary structures are also accompanied with an increasing rise in the incidence and mortality of CVDs.

Cardiomyocyte apoptosis is involved in the pathophysiological processes of various CVDs, including primary hypertension, ischemic heart disease (IHD), ischemia-reperfusion injury (IRI), myocarditis, cardiomyopathy, arrhythmia, heart failure, congenital heart disease (CHD), and the like. The dysfunction of cardiomyocyte apoptosis is an important mechanism for the occurrence of various severe CVDs. It has become important in drug research on CVDs to intervene in the progress of apoptosis, inhibit the occurrence of cardiomyocyte apoptosis, and save the heart and cardiac function. At present, statins, β-receptor blockers, angiotensin-converting enzyme (ACE) inhibitors, and the like are clinically used to inhibit cardiomyocyte apoptosis, but these drugs have side effects to varying degrees.

Due to the difficulty in collecting human cardiomyocyte samples, the short survival time of primary cardiomyocytes in vitro, and the ethical issues of research, it is almost impossible to directly use cardiomyocytes of a patient for CVD research. In recent years, with the development of induced pluripotent stem cell (iPSC) technology and the establishment of cardiomyocyte differentiation and purification methods, it has become possible to prepare and cultivate human cardiomyocytes in vitro. With the iPSC technology to induce cardiomyocytes in vitro, a sufficient number of human cardiomyocytes can be prepared in vitro to conduct various functional experiments and simulate the occurrence and development of CVDs, which greatly advances the research progress on mechanisms of CVDs.

At present, in vitro cardiomyocyte apoptosis models are generally induced by hydrogen peroxide ($H_2O_2$) or angiotensin II. Angiotensin II can induce cardiomyocyte apoptosis by activating an angiotensin II receptor, which is closer to the normal physiological process than the induction by $H_2O_2$. Therefore, angiotensin II is currently a common inducer for establishing cardiomyocyte apoptosis models.

The transcription factor gene MYOG encodes myogenin and is a member of the myogenic regulatory factor (MRF) gene family. The MRF family (including Myod, Myf5, Mrf4, and MYOG) plays a critical role in each stage of skeletal myogenesis. All members of this family share a conserved basic helix-loop-helix (bHLH) motif, which can bind to an E-box of a downstream gene, thereby activating the expression of a downstream muscle-specific gene. Studies have shown that MYOG plays a key role in muscle differentiation by controlling and initiating the fusion of myoblasts and the generation of muscle fibers. Studies in mice have shown that the deletion of the MYOG gene leads to severe defects in muscle differentiation, resulting in perinatal death. Therefore, MYOG is an essential regulatory factor for skeletal muscle development and is irreplaceable. At present, studies have confirmed that the MYOG gene is expressed in the hearts of mice, ducks, grass carp, Jinghai yellow chickens, and other animals, which may be related to the growth and development of myocardium. However, the expression of the MYOG gene in human cardiac tissues and the role of the MYOG gene in cardiac development have not been reported yet.

SUMMARY

By constructing angiotensin II-induced human induced pluripotent stem cell-differentiated cardiomyocyte (hiPSC-CM) apoptosis models in vitro, the present disclosure reveals for the first time the role of the transcription factor MYOG in the inhibition of cardiomyocyte apoptosis and provides a theoretical and scientific basis for drug research and development of cardiomyocyte apoptosis-associated CVDs. Thus, the cardiomyocyte apoptosis model becomes a new target for CVD drug research and development.

The present disclosure inhibits cardiomyocyte apoptosis by regulating the expression of the MYOG gene. Therefore, the drug can be a traditional drug or a gene-regulating drug, such as a packaged lentivirus capable of regulating the expression of the MYOG gene.

DETAILED DESCRIPTION OF THE EMBODIMENTS

In order to make the technical problems, technical solutions, and advantages of the present disclosure clearer, the present disclosure is described in detail below with reference to specific examples.

Figure 1:
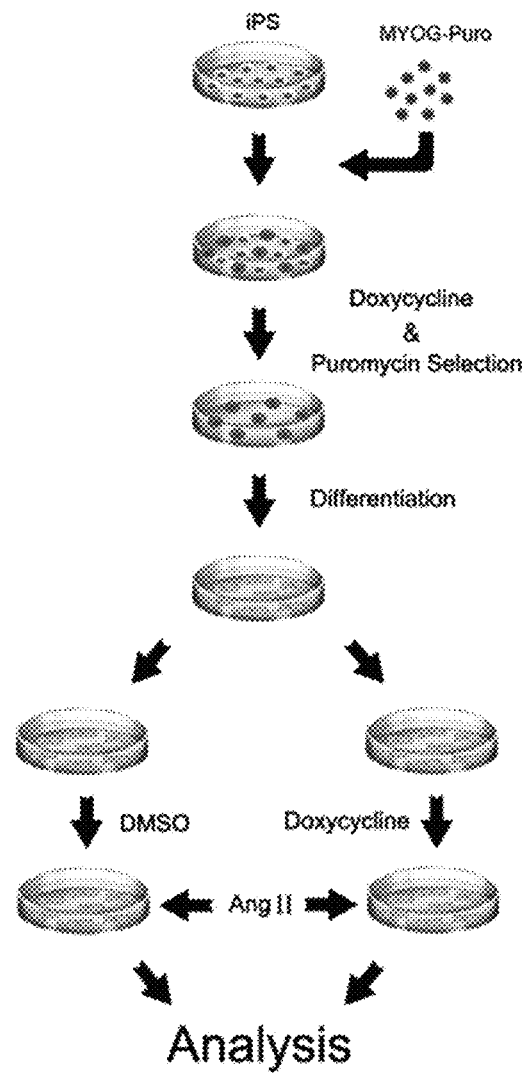
FIG. 1 is a technical flow chart of the present disclosure.

As shown in FIG. 1, the technical process of the present disclosure is as follows:
1. Construction of a pCW-MYOG vector.
2. Packaging of lentivirus.
3. Transfection of hiPSCs.
4. Differentiation of hiPSCs transfected with pCW-MYOG into cardiomyocytes and purification of the cardiomyocytes.
5. Induction of the expression of MYOG gene in hiPSC-MYOG cells with doxycycline hydrochloride (Dox) at a concentration of 2 μg/mL.
6. Induction of apoptosis of hiPSC-CM and pCW-MYOG-CM with angiotensin II at a concentration of 1 nM to 1 mM.
7. Determination of cell viability.
8. Determination of apoptosis.

Example 1 Acquisition of a hIPSC-MYOG Cell Line 1.1 Construction of a lentiviral expression vector: MYOG cDNA and a puromycin resistance gene were subcloned into a pCW-Cas9-Blast vector (Addgene, 83481) by a conventional molecular cloning method to replace the Cas9 and Blast genes in the original vector to obtain pCW-MYOG.

1.2 Packaging of Lentivirus 1.2.1 HEK293T cells were inoculated and cultivated with a D10 medium (DMEM medium+10% fetal bovine serum (FBS)) in a 6-well plate. When cell confluency reached 70% to 80%, the cells were ready for transfection.

1.2.2 The original medium was removed 1 h before transfection, and then a pre-warmed serum-free OptiMEM medium was added at 2 mL/well.

1.2.3 The transfection was conducted with the Lipofectamine 2000 reagent according to instructions. The HEK293T cells were co-transfected with pCW-MYOG (20 μg), pVSVg (10 μg) (Addgene), and psPAX2 (15 μg) (Addgene).

1.2.4 The medium was replaced with a D10 medium (DMEM medium+10% FBS+1% bovine serum albumin (BSA)) 6 h after the transfection.

1.2.5 The cells were further cultivated for about 60 h, and then a culture was collected and centrifuged at 3,000 rpm for 10 min at 4° C. to remove cell debris.

1.2.6 A resulting supernatant was filtered through a 0.45 μm low protein binding filter membrane (Millipore Steriflip HV/PVDF) to remove cell debris.

1.2.7 A resulting virus-containing filtrate was mixed with a 10% sucrose buffer (50 mM Tris-HCl, pH 7.4, 100 mM NaCl, 0.5 mM EDTA) in a volume ratio of 4:1, and the resulting mixture was centrifuged at 10,000 g and 4° C. for 4 h. The resulting supernatant was carefully discarded. The centrifuge tube was drained on absorbent paper for 3 min, then 1×PBS was added for resuspending, and the resulting suspension was stored at −80° C.

1.3 Transfection of hiPSCs 1.3.1 Cultivation of hiPSCs: The hiPSC DYR0100 (ATCC) was inoculated on a plate coated with Matrigel matrix (Corning, 354277), and then cultivated with STEMUP (Nissan Chemical Corporation). The STEMUP medium was changed every 2 days. iPSCs were passaged every 3 days, or the passage was conducted when a cell confluency reached 80% to 90%. During the passage, collected cells were rinsed once with 1×DPBS (Gibco, 14040133) and then treated with 0.5 mM EDTA (Invitrogen, 15575020) diluted by 1×DPBS (Gibco, 14190144) for 10 min at room temperature. A passage ratio was 1:3 to 1:6.

1.3.2 Transfection: The transfection was conducted when a confluency of hiPSCs reached 70% to 80% with a multiplicity of infection (MOI) of about 0.3 to 0.5. 24 h after the transfection. A medium was replaced with fresh STEMUP (with Dox at a final concentration of 2 μg/mL). 2 d later, the medium was replaced by STEMUP (with Dox 2 μg/mL+ puromycin (InvivoGen)) for screening. After 2 d to 3 d of screening, a transformation efficiency of about 30% was achieved. Single clones were picked and inoculated in different dishes to obtain the hiPSC-MYOG cell line.

Example 2 Dox-Induced Expression of MYOG 2.1 Induction: The expression of MYOG was induced by adding Dox (Sigma, D9891) at a final concentration of 2 μg/mL to STEMUP, and DMSO was used as a control. In the control group, only DMSO (denoted as C1) was added to STEMUP. In the experimental group, both DOX and DMSO were added to STEMUP, where DOX was first added to DMSO, and then a resulting mixture (denoted as C2) was added to STEMUP. A final concentration of DOX in STEMUP was 2 μg/mL, and the C1 and C2 were added at a same amount.

2.2 Total RNA extraction: The UN1Q-10 column Trizol total RNA extraction kit (Sangon Biotech, B511321-0100) was used to extract total RNA of the cells (a sample was treated with deoxyribonuclease I (DNase I, Sangon Biotech, B618252) for 30 min in advance).

2.3 Reverse transcription: RNA was reverse-transcribed with the reverse transcription kit iScript Reverse Transcription Supermix (Bio-Rad, 1708841).

2.4 qPCR detection of MYOG mRNA expression levels: According to the instructions of SsoAdvanced™ Universal SYBR® Green Supermix (Bio-Rad, 1725271), the PikoReal Real-Time PCR system (Thermo Fisher) was used to design primers with NAPDH as an internal reference, and then MYOG expression levels in hiPSC and hiPSC-MYOG (Dox-induced group and DMSO control group) were detected. Sequences of the primers were as follows:

```
MYOG-RT-F:
                                        (SEQ ID NO: 1)
GCCCAAGGTGGAGATCCT;

MYOG-RT-R:
                                        (SEQ ID NO: 2)
GGTCAGCCGTGAGCAGAT;

GAPDH-RT-F:
                                        (SEQ ID NO: 3)
TGGGTGTGAACCATGAGAAG;
and GAPDH-RT-R:
                                        (SEQ ID NO: 4)
GTGTCGCTGTTGAAGTCAGA.
```

Figure 2:
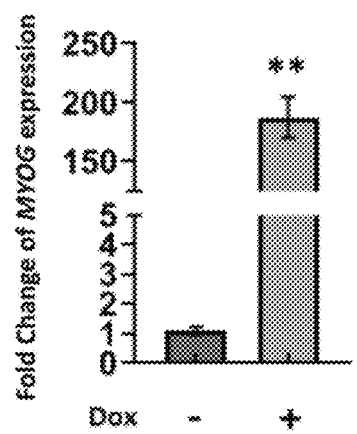
FIG. 2 shows the measurement results of MYOG expression levels in Example 2.

Result analysis: As shown in FIG. 2, the expression level of MYOG in the Dox-induced group was more than 100 times higher than the expression level of MYOG in the DMSO control group. The results showed that the hiPSC-MYOG cell line capable of expressing the MYOG gene at a high level was successfully constructed.

Example 3 Acquisition of hiPSC-CM/hiPSC-MYOG-CM 3.1 Differentiation of hiPSCs: hiPSCs were cultivated in an RPMI-BSA medium (RPMI1640 medium (HyClone, SH30027.01)+213 μg/mL L-ascorbic acid 2-phosphate magnesium (AA2P, Sigma, A8960)+0.1% BSA (Sigma, A1470)) with a small molecule CHIR99021 (Tocris, 4423, final concentration: 10 mM) for 24 h. Then the medium was replaced with the RPMI-BSA medium, and the cells were further incubated for 48 h. On day 4 of differentiation, a small molecule IWP2 (Tocris, 3533, final concentration: 5 μM) was added to the RPMI-BSA medium to treat the cells. 48 h later, the medium was replaced with the RPMI-BSA medium. Thus, hiPSCs were differentiated into hiPSC-CMs. In a subsequent experiment, cardiomyocytes were cultivated with an RPMI1640 medium and a 3% serum substitute (Gibco, 10828-028).

3.2 Purification of hiPSC-MYOG-CMs: hiPSC-CMs were purified by a metabolic selection method. A DMEM medium (sugar-free) (Gibco, 11966-025) with 0.1% BSA (Sigma, A1470) and 1× linoleic acid-oleic acid-albumin (Sigma, L9655) was used as a metabolic selection medium. The cells were cultivated with the metabolic selection medium for 3 d to 6 d. The medium was changed every 2 days. Cardiomyocytes obtained from purification by this method had a purity as high as 99%.

Example 4 Construction of Angiotensin II-Induced hiPSC-CM Apoptosis Models 2.1 Induction of hiPSC-CM apoptosis with angiotensin II: Purified hiPSC-CMs were cultivated in a cardiomyocyte medium (MedChemExpress, HY-13948) with angiotensin II at different concentrations (1 nM, 10 nM, 100 nM, 1 μM, 10 μM, 100 μM, and 1 mM), and the angiotensin II-containing medium was changed every 2 days.

Figure 3:
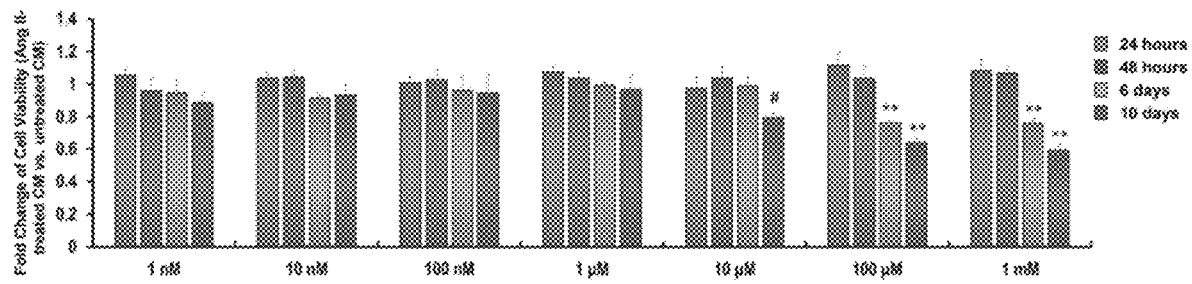
FIG. 3 shows the influence of an angiotensin II treatment on a cardiomyocyte viability in Example 4.

2.2 Verification of hiPSC-CM apoptosis:

2.2.1 A cardiomyocyte viability was detected with the PrestoBlue cell viability assay reagent (Invitrogen, A13261) at 24 h, 48 h, 6 d, and 10 d, and results are shown in FIG. 3.

Figure 4:
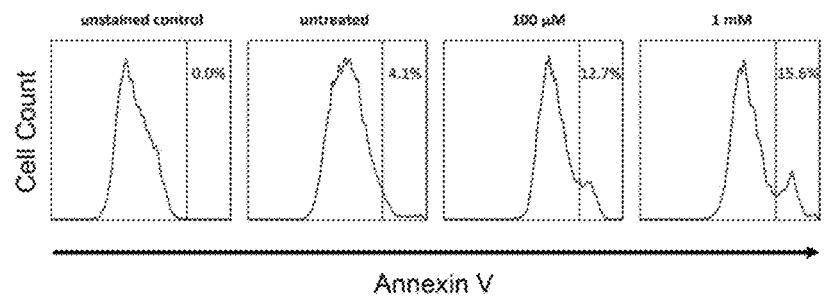
FIG. 4 shows the flow cytometry (FCM) results of apoptosis of cardiomyocytes treated with angiotensin II at different concentrations according to the Annexin V method.
Figure 5:
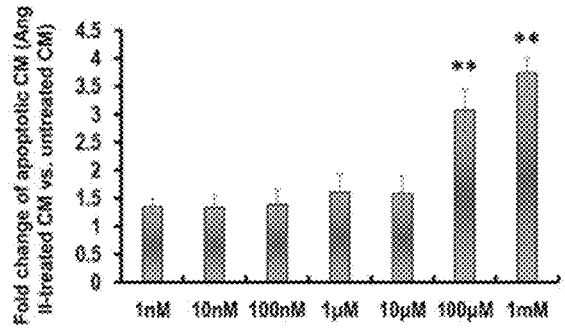
FIG. 5 shows the statistical results of apoptosis of cardiomyocytes treated with angiotensin II at different concentrations according to the Annexin V method.
Figures 6A, 6B, 6C:
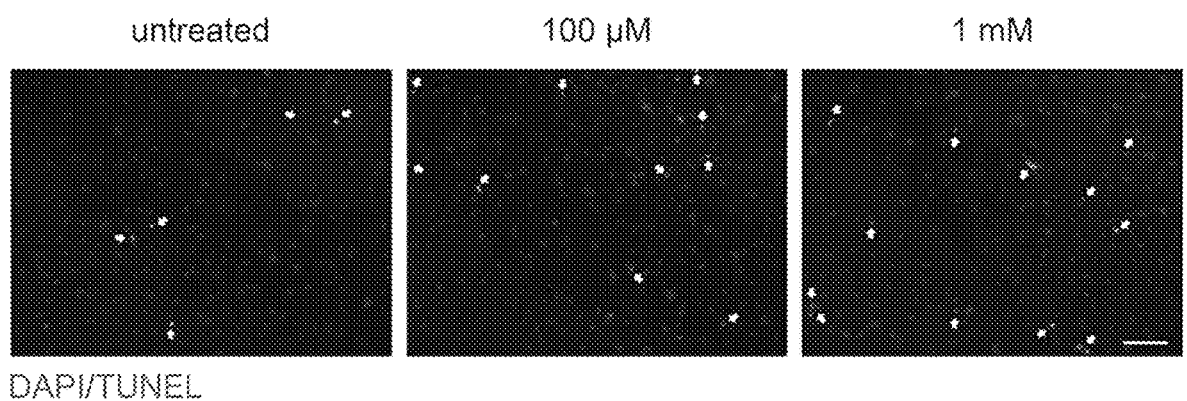
FIGS. 6A-6C show the immunofluorescence (IF) staining results of apoptosis of cardiomyocytes under the conditions of being untreated, treated with angiotensin II at 100 μM, treated with angiotensin II at 1 mM according to the TUNEL method, respectively.
Figure 7:
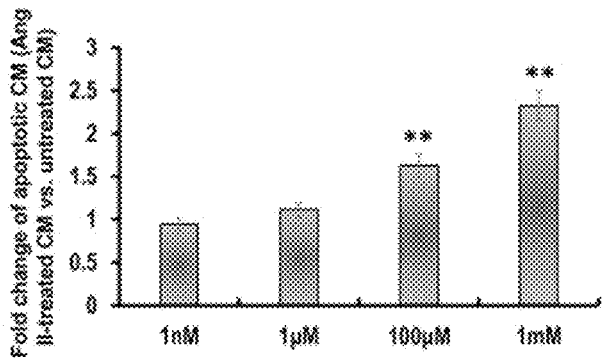
FIG. 7 shows the statistical results of apoptosis of cardiomyocytes treated with angiotensin II at different concentrations according to the TUNEL method.

2.2.2 The apoptosis of cardiomyocytes treated with angiotensin II (100 μM and 1 mM) and untreated with angiotensin II on day 10 was detected with the apoptosis assay kit Annexin V, Alexa Fluor™488 conjugate (Invitrogen, V13201). Cardiomyocytes were labeled with the apoptosis marker Annexin V and then assayed with a FACSAria™ II flow cytometer (BD). Results are shown in FIG. 4 and FIG. 5.

2.2.3 TUNEL test: The TdT in situ apoptosis detection kit (R&D Systems, 4812-30-K) was used to detect the apoptosis of cardiomyocytes treated with angiotensin II (1 nM, 1 μM, 100 μM, and 1 mM) and untreated with angiotensin II on day 10. Cardiomyocytes were digested, then added on a glass slide, and stained according to the kit instructions, and nuclei were labeled with DAPI.

Result analysis: The results of PrestoBlue cell viability assay (FIG. 3) showed that, after the long-term (6 d and 10 d) treatment of hiPSC-CMs with high-concentration angiotensin II (100 μM and 1 mM), the cell viability decreased significantly. The results of Annexin V and TUNEL tests (FIG. 4 to FIG. 7) showed that, after the long-term (10 d) treatment of hiPSC-CMs with high-concentration angiotensin II (100 μM and 1 mM), the proportion of apoptotic cells increased significantly. This indicates that the long-term treatment with high-concentration angiotensin II (100 μM and 1 mM) induced the apoptosis of hiPSC-CMs, and the cardiomyocyte apoptosis models were successfully constructed.

Example 5 Inhibition of MYOG on the Angiotensin II-Induced hiPSC-CM Apoptosis 5.1 Induction of hiPSC-MYOG-CM apoptosis with angiotensin II: Purified hiPSC-MYOG-CMs were divided into 4 groups (Ang II(+)&Dox(+), Ang II(+)&Dox(−), Ang II(−)&Dox(+), and Ang II(−)&Dox(−)) and then treated for 6 d with a Dox having a concentration of 2 μg/mL and an angiotensin II having a concentration of 1 mM.

Figure 8:
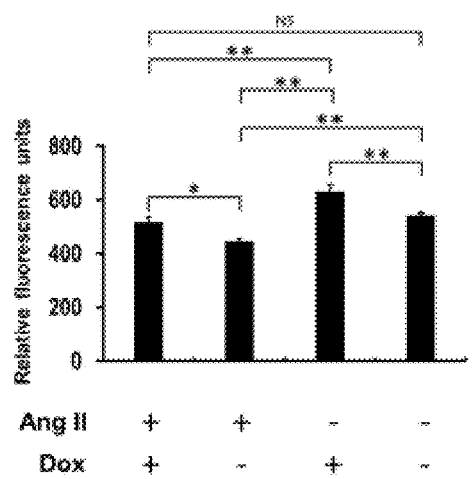
FIG. 8 shows the cardiomyocyte viability results tested by the PrestoBlue cell viability reagent.
Figure 9A:
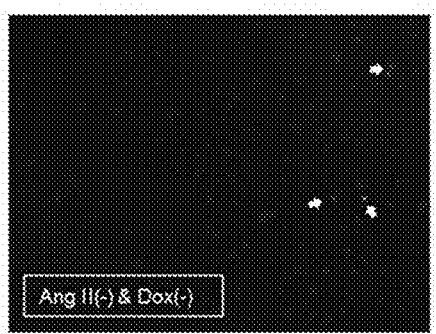
FIGS. 9A-9D show the IF staining results of angiotensin II-induced apoptosis inhibited by MYOG in four groups of Ang II(−)&Dox(−), Ang II(+)&Dox(−), Ang II(+)&Dox(+), and Ang II(−)&Dox(+), respectively.
Figure 9B:
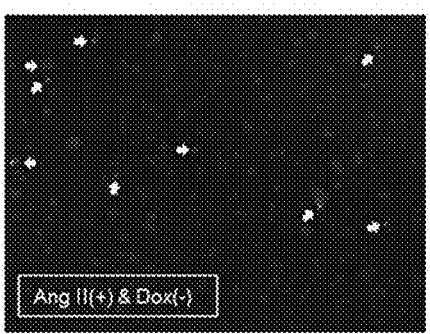
Figure 9C:
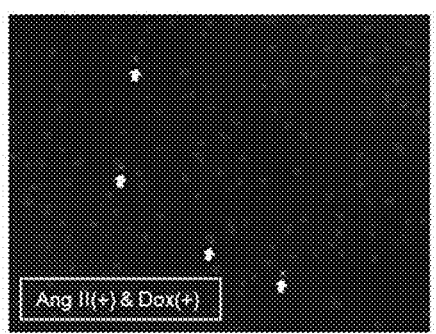
Figure 9D:
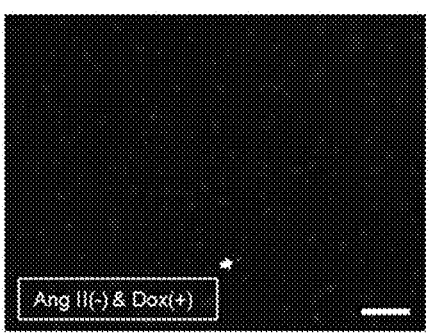
Figure 10:
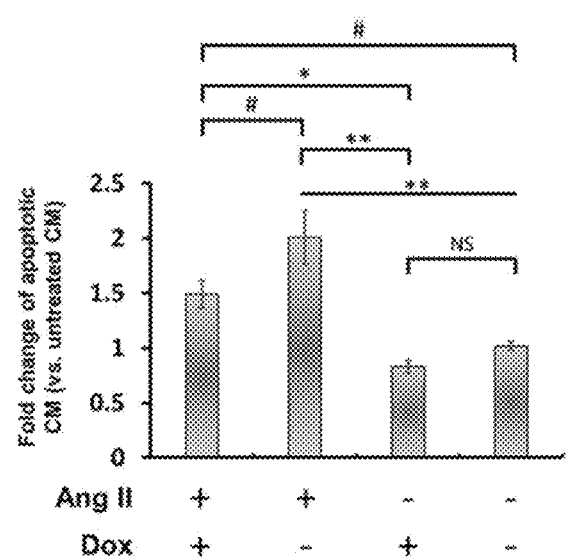
FIG. 10 shows the statistical results of angiotensin II-induced apoptosis inhibited by MYOG.

5.2 Cell viability detection: A cardiomyocyte viability was detected with the PrestoBlue cell viability assay reagent (Invitrogen, A13261), and results are shown in FIG. 8.

5.3 Apoptosis assay: TUNEL test: The TdT in situ apoptosis detection kit (R&D Systems, 4812-30-K) was used to detect the apoptosis of cardiomyocytes in the 4 groups (Ang II(+)&Dox(+), Ang II(+)&Dox(−), Ang II(−)&Dox(+), and Ang II(−)&Dox(−)). Cardiomyocytes were digested, then added on a glass slide, and stained according to the kit instructions. Nuclei were labeled with DAPI.

Result analysis: Compared with the Ang II(+)&Dox(−) group, the Ang II(+)&Dox(+) had a significantly-higher cell viability (FIG. 8) and a significantly-lower apoptotic cell proportion (the apoptotic cell proportions of the two groups were 1.49 times and 2.01 times the apoptotic cell proportion of the control group, respectively) (FIGS. 9A-9D and FIG. 10). This indicates that MYOG can inhibit the angiotensin II-induced hiPSC-CM apoptosis. In addition, there was no significant difference in the apoptotic cell proportion between the Ang II(−)&Dox(+) group and the Ang II(−)&Dox(−) group, indicating that MYOG has no influence on apoptosis in the absence of angiotensin II.

In summary:

(1) In the present disclosure, an iPSC-MYOG cell line is successfully constructed, and it is verified that Dox can induce the high expression of the MYOG gene in iPSC-MYOG cells.

(2) In the present disclosure, an angiotensin II-induced cardiomyocyte apoptosis model is established.

(3) The high expression of the MYOG gene can inhibit the cardiomyocyte apoptosis induced by angiotensin II.

The present disclosure discovers for the first time the effect of MYOG for inhibiting cardiomyocyte apoptosis and provides a new idea for drug research and development and clinical treatment of cardiomyocyte apoptosis-associated CVDs.

The above are preferred implementations of the present disclosure. It should be noted that a person of ordinary skill in the art may further make several improvements and modifications without departing from the principle of the present disclosure, but such improvements and modifications should also be deemed as falling within the protection scope of the present disclosure.

What is claimed is:

1. A method for inhibiting an angiotensin II-induced cardiomyocyte apoptosis comprising the step of administering a drug to promote a high expression of an MYOG gene in a human induced pluripotent stem cell-derived cardiomyocyte cell line transfected with pCW-MYOG (hiPSC-MYOG-CM).

* * * * *